(12) United States Patent
Meyer et al.

(10) Patent No.: US 6,736,793 B2
(45) Date of Patent: May 18, 2004

(54) SELF-SEALING DETACHABLE BALLOON

(75) Inventors: Ralph Meyer, West Branch, IA (US);
John D. Walker, Fairfax, VA (US);
Paul Volpini, Quincy, MA (US);
Michael J. Magliochetti, Iowa City, IA (US)

(73) Assignee: AMS Research Corporation, Minnetonka, MN (US)

( * ) Notice: Subject to any disclaimer, the term of this patent is extended or adjusted under 35 U.S.C. 154(b) by 274 days.

(21) Appl. No.: 10/012,734

(22) Filed: Nov. 5, 2001

(65) Prior Publication Data

US 2002/0049465 A1 Apr. 25, 2002

Related U.S. Application Data

(63) Continuation of application No. 09/241,582, filed on Feb. 2, 1999, now Pat. No. 6,312,405.

(51) Int. Cl.⁷ .................... A61M 29/00; A61B 17/12
(52) U.S. Cl. ............... 604/96.01; 604/164.01; 604/907; 206/571; 206/438; 206/363; 606/195
(58) Field of Search .................. 604/96.01, 103, 604/103.03, 907, 164.01, 164.03, 164.1, 921; 606/192, 194, 195; 206/210, 363, 438, 571

(56) References Cited

U.S. PATENT DOCUMENTS

| 3,834,394 A | 9/1974 | Hunter et al. |
|---|---|---|
| 3,978,863 A | 9/1976 | Fettel et al. |
| 4,026,296 A | 5/1977 | Stoy et al. |
| 4,213,461 A | 7/1980 | Pevsner |
| 4,327,734 A | 5/1982 | White, Jr. |
| 4,471,779 A | 9/1984 | Antoshkiw et al. |
| 4,517,979 A | 5/1985 | Pecenka |
| 4,527,293 A | 7/1985 | Eckstein et al. |
| 4,686,962 A | 8/1987 | Haber |
| 4,709,690 A | 12/1987 | Haber |
| 4,773,393 A | 9/1988 | Haber et al. |
| 4,802,479 A | 2/1989 | Haber et al. |
| 4,819,637 A | 4/1989 | Dormandy, Jr. et al. |
| 4,832,680 A | 5/1989 | Haber et al. |
| 4,950,257 A | 8/1990 | Hibbs et al. |
| 4,968,294 A | 11/1990 | Salama |
| 5,181,921 A * | 1/1993 | Makita et al. ........... 604/99.02 |
| 5,222,970 A | 6/1993 | Reeves |
| 5,300,032 A | 4/1994 | Hibbs et al. |
| 5,306,226 A | 4/1994 | Salama |
| 5,339,833 A | 8/1994 | Berthiaume et al. |
| 5,361,777 A | 11/1994 | Sellers |
| 5,411,475 A | 5/1995 | Atala et al. |
| 5,437,603 A | 8/1995 | Cerny et al. |
| 5,451,235 A | 9/1995 | Lock et al. |
| 5,456,713 A | 10/1995 | Chuter |
| 5,593,419 A | 1/1997 | Segar |
| 5,639,796 A | 6/1997 | Lee |
| 5,779,672 A * | 7/1998 | Dormandy, Jr. .......... 604/99.04 |
| 5,830,228 A | 11/1998 | Knapp et al. |

* cited by examiner

Primary Examiner—Manuel Mendez
Assistant Examiner—Michael M Thompson
(74) Attorney, Agent, or Firm—Jeffrey J. Hohenshell

(57) ABSTRACT

A detachable balloon system includes an inflatable balloon with a self-sealing valve. The balloon has an elastomeric membrane and a proximal opening. The self-sealing valve is made up of a valve body for receiving an inflation instrument to inflate the balloon. The valve body is preferably formed of a biocompatible elastomeric material and includes a base portion and a sealing portion. The base portion is bonded to the elastomeric membrane so as to seal the proximal opening of the balloon. The sealing portion is located within the balloon and extends distally from the base into the balloon. The sealing portion is compressibly sealable in response to a pressure within the balloon following inflation of the balloon and removal of the inflation instrument. A balloon dispenser for housing a balloon prior to receipt of an inflation instrument is also described.

3 Claims, 4 Drawing Sheets

SELF-SEALING DETACHABLE BALLOON

RELATED APPLICATIONS

This application is a continuation of U.S. patent application Ser. No. 09/241,582 filed Feb. 2, 1999, now U.S. Pat. No. 6,312,402, which is incorporated herein by reference.

BACKGROUND OF THE INVENTION

The technical field of this invention is surgical instruments and, in particular, inflation catheters and detachable balloon systems for implanting structures in vivo.

Balloon catheters are used in a variety of medical procedures. Balloon catheters have been used extensively in the cardiovascular area, for example, to occlude vessels in certain types of surgery and to expand blood vessels as in an angioplasty procedure. Inflation catheters carrying detachable balloons have been used to treat urinary incontinence as disclosed in, e.g., U.S. Pat. No. 4,832,680, issued May 23, 1989; U.S. Pat. No. 4,802,479, issued Feb. 7, 1989; and U.S. Pat. No. 4,773,393, issued Feb. 27, 1988. These patents describe an extensible, inflatable containment membrane which is implanted between the urethra and the subcutaneous corpus spongiousum of a patient to overcome urinary incontinence.

Inflation catheters carrying detachable balloons have also been used in endoscopic or cystoscopic methods to treat vesicouretal reflux. In such a procedure, described in U.S. Pat. No. 5,304,123, a needle is directed through a cystoscope and inserted into the subureteral region of a refluxing bladder to establish a pocket. A catheter or similar delivery device can be inserted into this pocket in the subureteral region carrying a balloon. The balloon can then be inflated and sealed. In one embodiment, the balloon is delivered on an inflation catheter through the cystoscopic needle. The uninflated balloons must be sized to fit on the tip of the catheter and for delivery within the cystoscopic needle. Once delivered to the desired area within a patient's body, the balloon is inflated or filled with a biocompatible material supplied through the catheter. The catheter is then withdrawn leaving the balloon in place. Preferably, the balloon includes a sealing mechanism so that the balloon seals itself upon inflation and removal of the catheter.

Additional endoscopic procedures involving inflation catheters with detachable balloons are disclosed in U.S. Pat. No. 5,411,475, issued May 2, 1995. According to this patent, a scope is provided for directly visualizing a target site in vivo. The scope includes a viewing means, a sheath, and a positioning element extending through the sheath. An uninflated, detachable balloon attached to a catheter is passed through the lumen of the positioning device, such as a hollow needle, to the target site. The balloon is then inflated and detached at the target site. The disclosed system and method can be used in a variety of medical procedures including birth control procedures.

Balloons useful in these procedures must be very small. In some procedures, a 19 gauge needle small enough to fit within standard cystoscopic equipment is used as a cystoscopic positioning device. In one system, a thin walled cystoscopic needle has a 19 gauge outer diameter and has an inner diameter of a standard 18 gauge needle (i.e., 0.036 inches). Accordingly, a balloon useful for such procedures must be readily passable though the inner lumen of this needle. The balloon is also preferably selfsealing upon inflation and detachment from the catheter. The balloon should also be detachable from the catheter with a detachment force that is appropriate to the application. The detachment force must be high enough to allow the balloon to inflate without premature detachment, and low enough to allow the catheter to be readily withdrawn without dislodging the inflated balloon from the target site.

One example of a balloon known in the art is provided in U.S. Pat. No. 4,819,637, issued Ap. 11, 1989. This balloon includes a valve base having a smooth surface cylindrical bore extending therethrough for attachment to a catheter and a "duck-bill" type valve attached to the valve base. An additional detachable balloon is described in U.S. Pat. No. 4,832,680. That balloon is apparently larger than balloons delivered through a cystoscopic needle (it is delivered through a trocar) and includes a solid valve core that is prestressed by a surrounding compression band and a needle stop. The core and compression band are also surrounded by titanium tubing that forms a needle stop to prevent damage to the balloon. The balloon membrane is bonded to the compression band.

Known balloons perform poorly when miniaturized for delivery through small lumens, such as a cystoscopic needle, or they are expensive to make in miniature or both. Accordingly, it is an object of the present invention to provide a low cost, easy to manufacture, highly efficient miniature balloon for detachable delivery in vivo.

SUMMARY OF THE INVENTION

The invention provides a detachable balloon system including an inflatable balloon having a self-sealing valve. The balloon has an elastomeric membrane and a proximal opening. The self-sealing valve is made up of a valve body for receiving an inflation instrument to inflate the balloon. The valve body is preferably formed of a biocompatible elastomeric material and includes a base portion and a sealing portion. The base portion is bonded to the elastomeric membrane so as to seal the proximal opening of the balloon. The sealing portion is positioned internally within the balloon membrane and extends distally from the base portion into the balloon. The sealing portion is compressibly sealable in response to a pressure within the balloon following inflation of the balloon and removal of an inflation instrument.

The size of the self-sealing balloon and valve of the invention may readily be scaled down for even the smallest applications while maintaining an ease of manufacture that is unknown in the art. In addition, the balloon and valve of the invention can reliably reseal after removal of an inflation instrument, even under high inflation pressure conditions, regardless of balloon size.

In one embodiment, the base and sealing portions of the valve body are both cylindrical and the sealing portion has a smaller diameter than the base. A guide opening can also be formed in the proximal surface of valve body for guiding an inflation instrument to the center of the valve body. The valve body may also be provided with a pierce, slit or other opening extending longitudinally therethrough. A guide portion may also be provided on the valve body integrally formed with and proximal to the base. When the guide portion has a larger diameter than the base, a distal facing ledge, convenient for locating the balloon with respect to the valve body, is provided on the guide portion.

Generally, the benefits provided by the detachable balloon of the invention are greatest where the balloon has an uninflated diameter of about 0.010 to 0.125 inches and more preferably where the uninflated diameter of the balloon is no greater than about 0.060 inches (including uninflated diameters of less than 0.010 inches). Balloons of the invention may generally have a filled volume of about 10 ccs or less, and more preferably about 0.1 to 1.0 ccs.

A balloon dispenser for housing a balloon prior to receipt of an inflation instrument is also provided. The balloon dispenser includes a balloon seating element sized to allow the balloon to rest in the seating element, a guideway channel for guiding an inflation instrument into mating alignment with the balloon, and an element responsive to external pressure for holding the balloon steady against longitudinal movement with respect to the inflation instrument. In one embodiment, the element responsive to external pressure for holding the balloon includes a solid portion proximate to the balloon and being deflectable in response to external pressure so as to compress the balloon into the balloon seating element.

BRIEF DESCRIPTION OF THE DRAWINGS

The invention will be more fully understood by reference to the following detailed description when considered in conjunction with the accompanying drawings, in which.

DETAILED DESCRIPTION

Figure 1:
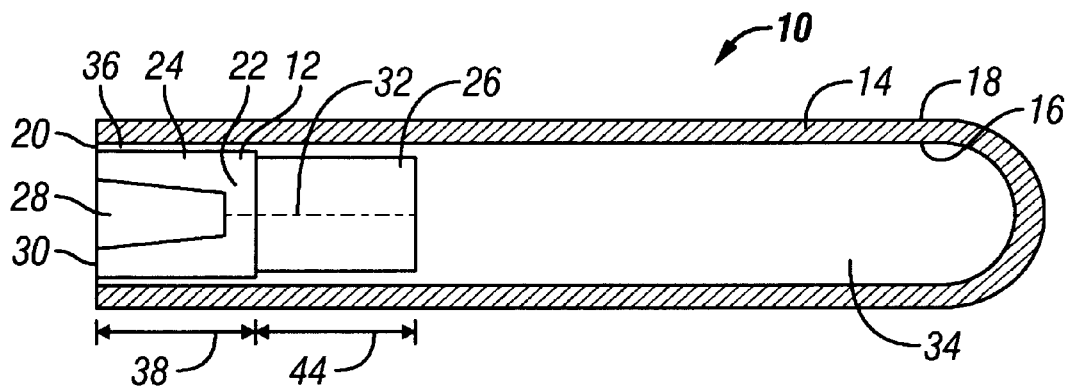
FIG. 1 illustrates, partially in section, a detachable balloon having a self-sealing valve of the invention.
Figure 2:
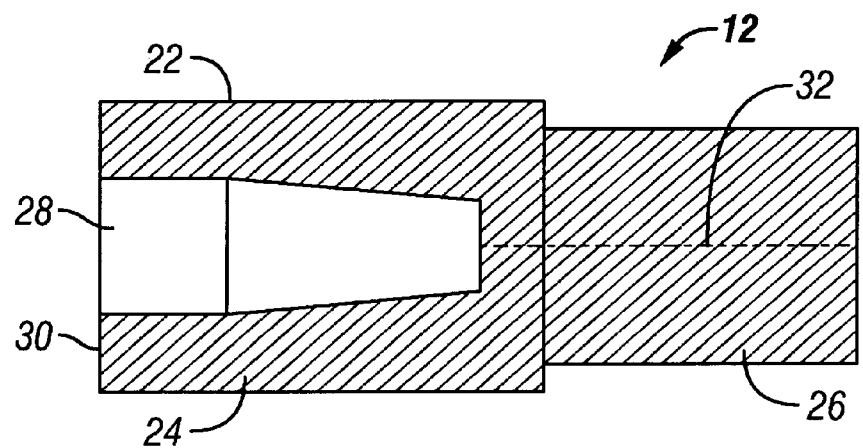
FIG. 2 illustrates, in cross-section, the self-sealing valve of FIG. 1.

A detachable balloon 10 having a self-sealing valve 12 is illustrated in FIG. 1, with the valve shown in more detail in FIG. 2. Balloon 10 is an inflatable balloon and includes an elastomeric membrane 14 having inner and outer surfaces 16, 18 and a proximal opening 20. The elastomeric membrane 14 may be made from any biocompatible elastomeric material, including for example cross-linked polydimethylsiloxane, polyurethane, hydrogel, PET and others, and should be of an appropriate thickness such that the balloon 10 has a suitable rupture or burst strength for the intended inflatable in vivo application. In one embodiment, the elastomeric membrane is made of silicone and has a thickness of about 0.007 inches.

A self-sealing valve 12 is provided in conjunction with balloon 10. The self-sealing valve 12 is made up of a unitary valve body 22 having a proximal base portion 24 and an integrally formed distal sealing portion 26 extending distally from the base 24. Base 24 can include a guide opening 28 at its proximal end 30 for guiding a distal end of a catheter to the center of the valve body 22. Guide opening 28 may be cylindrical, conical, or a combination. Valve body 22 can also be provided with a pierce 32, slit or other opening extending longitudinally through the valve body. Pierce 32 may be provided with a lubricant, such as silicone oil which can be inserted into pierce 32 using a syringe, in order to ease the entry of an inflation instrument through the valve body. In use, balloon 10 is loaded onto a distal end of a catheter by guiding a hollow tube at the end of the catheter into the guide opening 28 and inserting the hollow tube through valve body 22 into the open area 34 distal to the valve body 22 within the uninflated membrane 14.

The base 24 of the valve body 22 is bonded to the balloon membrane 14 using an adhesive or bonding compound 36 in proximity to the proximal opening 20 of the balloon 10. Bonding agents 36 useful for coupling the base 24 to the membrane 14 include Room Temperature Vulcanizing (RTV) silicone, heat curing silicone and UV curing polyurethane among others. While other configurations are possible, coupling the base 24 to the inner surface 16 of balloon 10 provides for easier manufacture, and thus reduced cost and increased reliability, of miniature balloons. Alternatively, the balloon membrane 14 can be bonded to the base by heat or chemical reaction. The distal sealing portion 26 of the valve body 22 is not adhesively coupled to the membrane 14 and, in one embodiment, the sealing portion 26 and the base portion 24 are both cylindrical with the sealing portion having a smaller diameter than the base portion.

This configuration allows for adhesive 36 to be readily applied to the base portion 24 only and for uncomplicated insertion of the valve body 22 into the open end 20 of the balloon 10 during manufacture. Alternatively, adhesive 36 can be applied to the inner surface 16 of the membrane 14 and the valve body 22 can be inserted into the proximal opening 20 of the balloon without having the sealing portion 26 contact the adhesive 36.

Adhesive 36 is applied along the length of base portion 24. The adhesive 36 is preferably biocompatible, especially where the proximal edge of the adhesive is exposed outside the balloon 10. The length 38 of the base portion 24 should be sufficient to allow for enough adhesive 36 to create a barrier at the open end 20 of the balloon 10 so that the balloon can be inflated without leakage through the bonded area and will preferably create a bond between the membrane 14 and the base portion 24 that is stronger than the rupture or burst strength of the membrane. The base 24 should also have a great enough length 38 so that, considering the cross-sectional size of the base and of any guide opening 28 formed therein, the base portion 24 does not deform so as to compromise the function of the valve body 22 under inflation conditions.

Additional features or structures, while not necessary to implement the detachable balloon of the invention, may be added to further ensure that adhesive is applied only between the base 24 and the balloon membrane 14. For example, a trough could be provided around the circumference of base 24, and that trough could be filled with adhesive before joining balloon membrane 14 to the base. In addition, a flange could be added on the circumference of base 24, or between base 24 and sealing portion 26, with adhesive applied to the flange before joining the balloon membrane 14 to base 24. In this configuration, the flange would apply adhesive only to portions of the balloon membrane 14 that would contact base 24.

Figure 3:
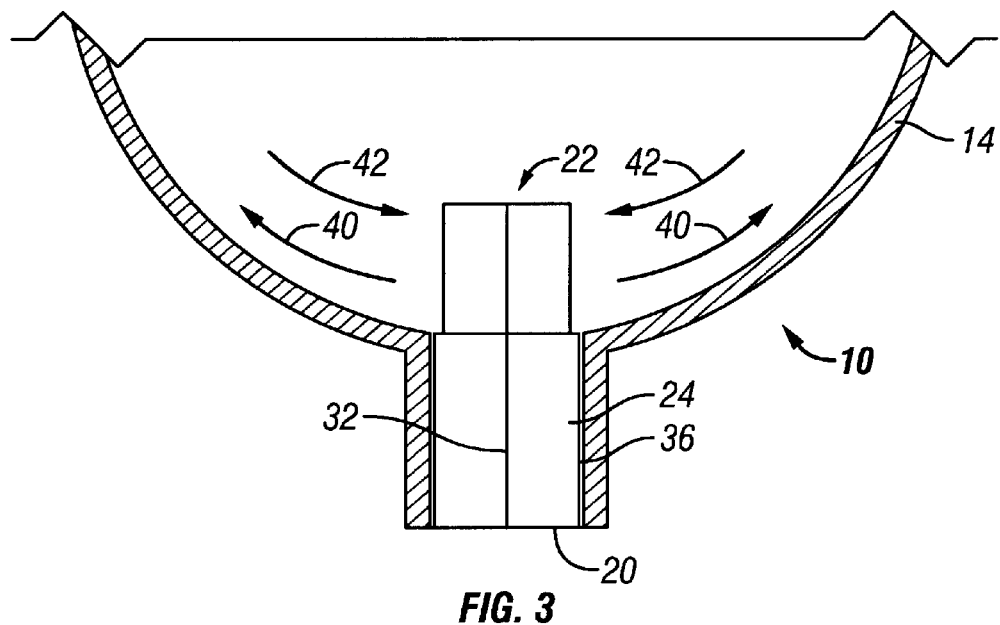
FIG. 3 illustrates, partly in section, how a self-sealing valve of the invention works under inflation conditions.

The operation of valve body 22 under inflation conditions is illustrated in FIG. 3. The membrane 14 has been expanded to reflect the effect of inflation on the balloon 10 and arrows 40, 42 indicate forces applied to the valve body 22 as a result of the inflation. Inflation causes the membrane 14 to pull outwardly 40 on the base portion 24 of the valve body 22. The inflation pressure however, tends to compress 42 the sealing portion 26 of valve body 22 to close pierce 32 after removal of an inflation instrument.

The length 44 (FIG. 1) of the sealing portion must be sufficiently large, in combination with the properties of the material selected for the valve body 22, to allow the inflation pressure to compressibly seal the sealing portion 26 upon removal of a catheter tube after inflation. One advantageous feature of the balloon and valve of the invention is that increased pressure within the balloon results in an increased closing force on the valve, reducing the possibility of undesired leakage through the valve under higher pressures.

The valve body 22 can be integrally formed from an elastomeric material such as silicone. Silicone is an elastomeric material that exhibits a high degree of surface adhesion, allowing two separate silicone surfaces to form a primary bond when joined together over a given amount of time. For this reason, silicone can be described as having a self-sealing or resealing capability. Accordingly, removal of a catheter tube from the valve body 22, combined with the inflation pressure effects, causes self-sealing in the valve body 22 of the invention.

The size of balloon 10 may be varied within the scope of the invention without making the sealing portion longer or shorter, however, the sealing portion length 44 (FIG. 1) may be varied to account for higher or lower inflation pressures within balloon 10. Changing material properties may also effect the performance of the sealing portion 26 without incurring leakage through the valve body 22. For example, increasing the durometer of the sealing portion 26 material will increase the detachment force required to detach the balloon 10 from an inflation catheter.

In one embodiment, the valve body, is formed, in part or in whole, from a hydrophilic hydrogel. Such hydrophilic hydrogel polymers include polyvinyl pyrrolidone, polyvinyl alcohol, polyhydroxyethyl acrylate or methacrylate, polyhydroxypropyl acrylate or methacrylate, and copolymers of these with each other or with acrylic or methacrylic acid, acrylic or methacrylic esters or vinyl pyridine. The hydrogel is preferably hypoallergenic and uses a cellulosic, polyurethane, or polyacrylate base. Using hydrogel for the valve body 22 results in decreased resistance when inserting a catheter tube. In addition, hydrophilic materials have a strong affinity for binding or absorbing water which results in controllable swelling. When the balloon is inflated or filled with a material that includes water, such as saline for example, the hydrophilic valve body will attract water and will swell, increasing the sealing effect of the valve body. By tailoring the hydrogel chemistry, one can fine tune or predetermine the amount of water absorption, thus controlling the amount of swelling. Therefore, by varying the amount of water absorbed by the hydrogel, differing detachment forces for detaching the balloon from an inflation catheter may be achieved.

Figure 4:
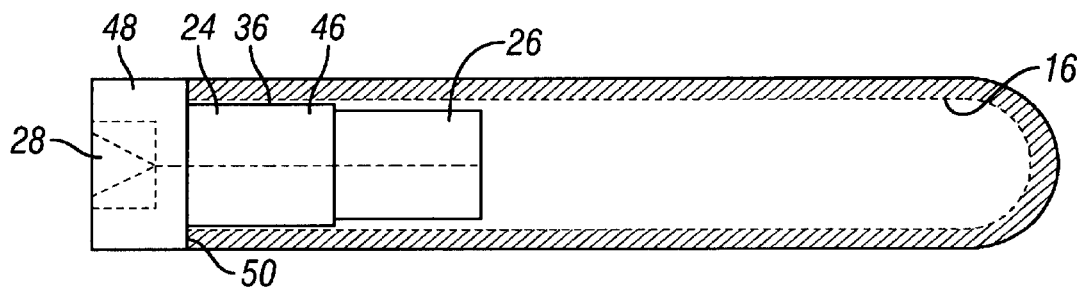
FIG. 4 illustrates, partly in section, an additional balloon having a self-sealing valve of the invention.
Figure 5:
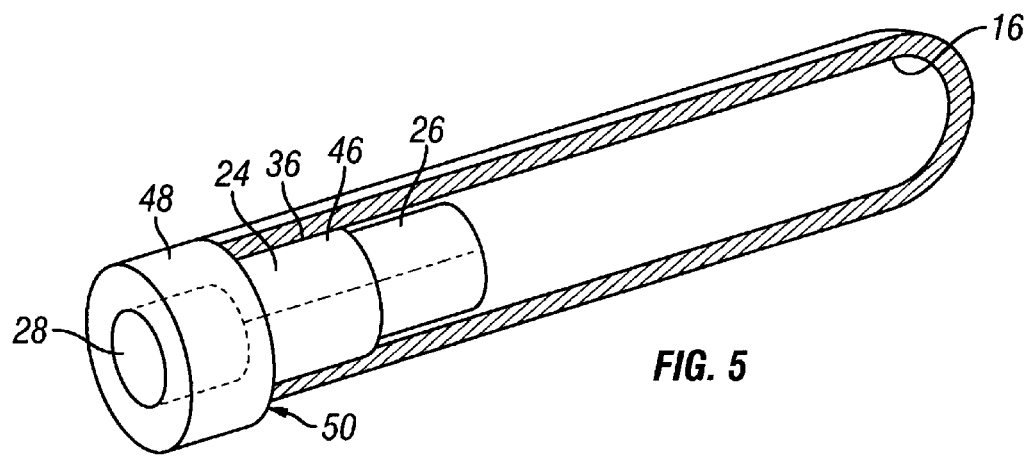
FIG. 5 illustrates, in perspective, the balloon having a self-sealing valve of FIG. 4.

An additional detachable balloon of the invention similar to balloon 10 of FIG. 1 but having valve body 46 is illustrated in FIGS. 4 and 5. Valve body 46 of this balloon includes a guide portion 48 in addition to base 24 and sealing 26 portions. The guide portion 48 is integrally formed with the base 24 and has a larger diameter than the base, the larger diameter resulting in a distal facing ledge 50 adjacent to the base 24. Using valve body 46, the balloon can be manufactured by coating the base 24 or the inner surface 16 of the balloon with adhesive 36 and inserting valve body 46 into the open end of the balloon until ledge 50 meets the proximal edge of the balloon. This method of manufacture is particularly advantageous for reliably producing miniature balloons at low cost. In addition, guide opening 28 can be formed in guide portion 48 rather than in base portion 24, allowing greater structural integrity in base portion 24 in response to forces applied on the base in an inflated state.

The detachable balloon system of the invention can be readily manufactured even when reduced to miniature sizes. For example, a valve body such as valve body 22 of FIG. 2, formed of silicone, may generally be produced having a base portion length 38 of 0.070 inches, a base portion diameter of 0.047 inches, a sealing portion length 44 of 0.050 inches and a sealing portion diameter of 0.038 inches. In the embodiment of FIGS. 4 and 5, the guide portion 48 may have a length of approximately 0.030 inches. A balloon membrane, such as balloon membrane 14, useful with valve body 22 can also be formed of silicone and have an uninflated outer diameter of 0.060 inches and a wall thickness of 0.007 inches. The length of the balloon 10 is driven primarily by desired final balloon volume, but the length should provide adequate empty space 34 for a catheter tube to be inserted through the valve body 22 without breaching the distal end of the balloon. For example, a 0.9 cc balloon for the system described herein would have a length of approximately 0.300 inches.

While specific dimensions have been provided, a person of ordinary skill in the art will readily appreciate that the detachable balloon of the invention may be scaled to other sizes consistent with the teachings of the invention. Generally, the benefits provided by the detachable balloon of the invention are greatest where the balloon has an uninflated diameter of about 0.010 to 0.125 inches and more preferably where the uninflated diameter of the balloon is no greater than about 0.060 inches (including uninflated diameters of less than 0.010 inches). Balloons of the invention may generally have a filled volume of about 10 ces or less, and more preferably about 0.1 to 1.0 ccs.

Balloons of the invention may be used in a variety of medical procedures. For example, the balloons of the invention may be used in the endoscopic and cystoscopic methods of U.S. Pat. Nos. 5,304,123 and 5,411,475 which are hereby incorporated by reference. In those methods, a scope having an endoscopic lense also includes a working channel having a positioning device. The positioning device may be a hollow needle such as a cystoscopic needle through which a balloon may be passed. Alternatively, a positioning device for use with the present invention may be a sheath in the working channel of a scope through which a tissue penetrating needle may be passed to create an opening in the target tissue. The scope can, for example, be passed through the urethra (transurethral delivery) to a target site between the urethra and the subcutaneous corpus spongiousum. The needle may then be removed and a catheter carrying a detachable balloon of the invention may be delivered through the sheath to the target site and inflated.

The balloon of the invention may also be used in a periurethral method wherein a hollow sheath carrying a needle is passed through submucosa tissue in a direction parallel to the patient's urethra. A cystoscope can be used to visualize the movement of the tissue and thus the movement of the sheath. In addition, a depth marker can be provided on the sheath. Once the sheath reaches the target site, the needle can be removed from the sheath and a balloon may then be directed to the target tissue on an inflation catheter through the sheath. In a variation on the periurethral approach, the target site may be approached transvaginally and through the vaginal wall.

Figure 6:
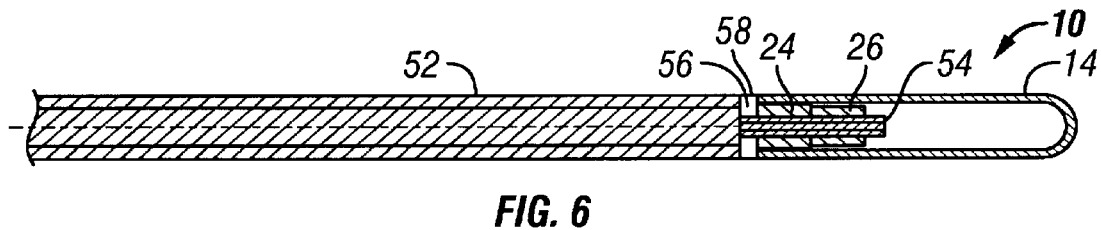
FIG. 6 illustrates a detachable balloon of the invention mounted onto a catheter.

An inflation catheter 52 useful with a balloon of the invention is illustrated in FIG. 6. Catheter 52 includes a blunt hollow tube 54 extending distally from the distal end 56 of the catheter. Catheter 52 preferably includes a distal facing ledge 58 on the distal end 56 of the catheter for abutting the proximal end of a detachable balloon. Hollow tube 54 should be long enough to extend through the valve body of a balloon, but short enough so as not to contact the inner surface of the balloon membrane. Using a hollow tube 54 with a blunt tip reduces the chance that the tube 54 will penetrate the balloon membrane. When a hollow blunt tipped tube is used with balloon 10, valve body 22 is preferably provided with pierce 32 to reduce the chance that the hollow tube 54 will puncture, tear or core out the valve body 22.

Figure 7:
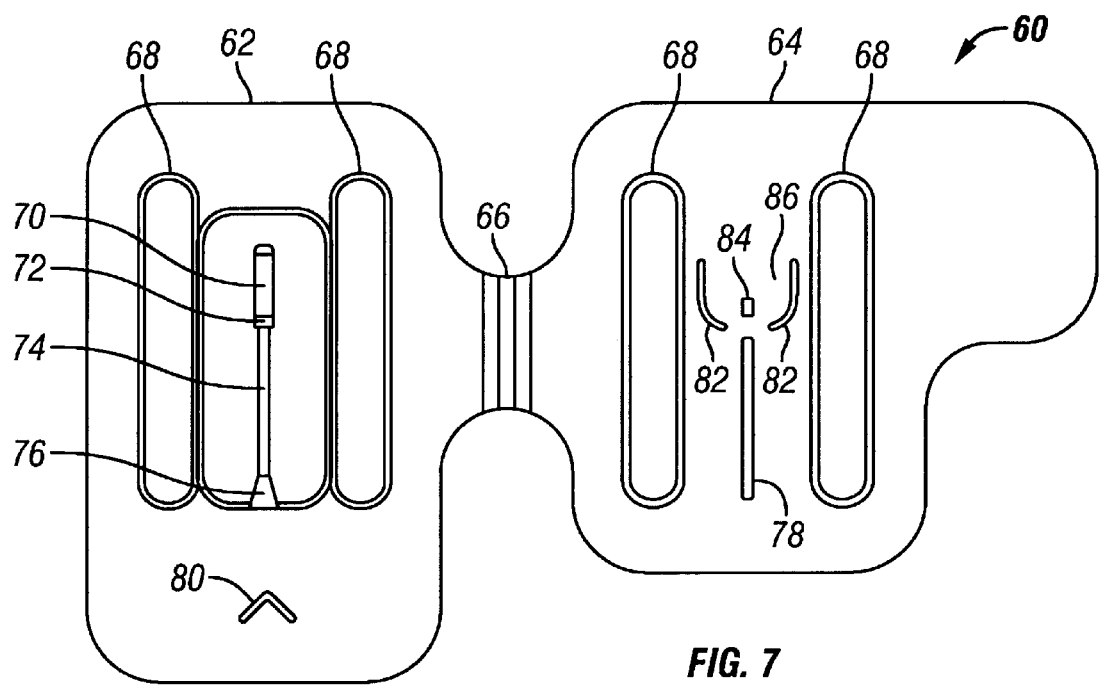
FIG. 7 illustrates a balloon dispenser useful the detachable balloons of FIGS. 1 and 3–6 in an open position.
Figure 8:
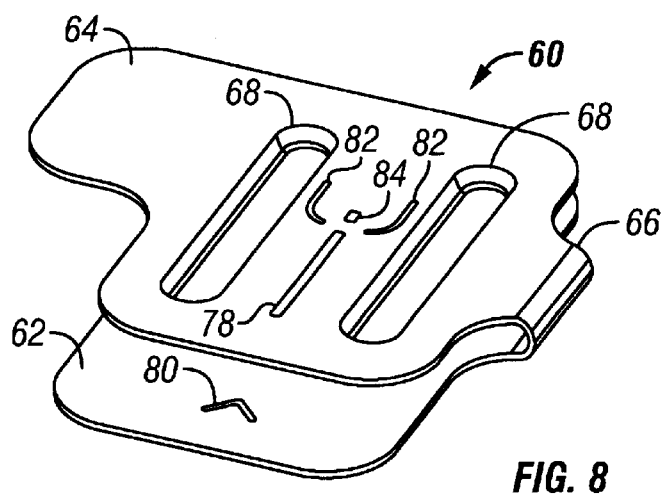
FIG. 8 illustrates the balloon dispenser of FIG. 7 in a closed position.

In one embodiment, a balloon of the invention is provided in a balloon dispenser such as balloon dispenser 60 illustrated in FIGS. 7 and 8. Because of the small size of the balloons of the invention, it can be difficult for a surgeon, especially when wearing gloves, to load a balloon onto a catheter so that the balloon is centered on the catheter tube and the balloon membrane is not penetrated by the catheter tube. In addition, balloons of the invention are preferably not provided in prepackaged form attached to a catheter. Such a preform, especially if stored for a significant period of time before use, can result in the elastomeric valve body taking shape around the catheter tube so that removal of the tube from the valve body leaves behind a cylindrical bore in the valve body that is difficult to reseal resulting in subsequent balloon leakage. For at least these reasons, it is desirable to provide balloons in a balloon dispenser 60 that allows easy mounting of a detachable balloon on a catheter in a sterile environment shortly before deployment of the balloon in vivo.

Exemplary balloon dispenser 60, having two sides 62, 64 connected by a hinge-like connecting member 66, is illustrated in FIG. 7 in an open position, and in FIG. 8 in a closed position. Each side is provided with mating snap members 68 which cause the dispenser 60 to releasably lock into a closed position when the sides 62, 64 are pressed together. Dispenser 60 includes a balloon seating area 70 shaped and dimensioned to allow a balloon to be seated therein. Preferably, the balloon only rests in the seating area 70 and is not compressed to fit into the seating area which might cause an elastomeric balloon valve to change shape over time.

For example, for a balloon having an uninflated diameter of 0.060 inches, balloon seating area 70 might have a diameter of 0.063 inches. In addition, an area of slight compression 72, having a diameter of say 0.058 inches, can be provided in the balloon seating area 70. Dispenser 60 also includes a guideway 74 that extends from the balloon seating area 70 and communicates with the outside of the dispenser through a funnel 76. The funnel 76 helps a surgeon to guide a catheter into guideway 74 which leads to the center of the balloon valve. A viewing channel 78 may also be provided to allow the surgeon to see when the catheter has moved through the guideway 74 and mated with a balloon. A visual indicator 80 may also be provided outside the guideway 74 to indicate where the catheter is to enter the guideway 74.

Dispenser 60 can be provided with a pressure means that allows a surgeon to forcibly capture a balloon that is resting in the balloon seating area 70 so that a catheter can be mated with a balloon without moving the balloon longitudinally away from the catheter in response to contact. For example, dispenser 60 is provided with relief channels 82 and a balloon retaining channel 84. When a balloon is loaded in the balloon seating area 70 and the dispenser is closed, a surgeon can apply pressure by squeezing a solid portion 86 of the dispenser 60 in the vicinity of the relief channels 82. The solid portion 86 will deflect to squeeze the balloon, with a portion of the balloon extending into the balloon retaining channel 84. This will temporarily prevent a balloon from moving longitudinally in response to the presence of a catheter.

Balloons of the invention can be prepackaged in a dispenser for distribution to hospital or surgeons and may be contained in sterile or sterilizable packaging. A surgeon can use a balloon and dispenser by holding the dispenser 60 in one hand and inserting a catheter such as catheter 52 with the other hand into guideway 74 through funnel 76. The surgeon will be able to visualize the catheter in the guideway 74 through viewing channel 78. At any time before contacting the balloon with the catheter, the surgeon can squeeze the dispenser 60 so as to capture the balloon against longitudinal motion. The surgeon can then mate the catheter to the balloon by inserting the catheter until the distal facing ledge 58 meets the proximal edge of the balloon and the catheter tube 54 extends through the valve body 22. The surgeon can then open the dispenser 60 and use the balloon and catheter in any procedure outlined herein, or any other procedure in which the balloon and catheter may be appropriate.

It will be understood that the foregoing is only illustrative of the principles of the invention, and that various modifications can be made by those skilled in the art without departing from the scope and spirit of the invention. In particular, various features of the balloon and dispenser systems described herein may be combined within the invention. All references cited herein are expressly incorporated by reference in their entirety.

What is claimed is:

1. A detachable balloon system for in vivo placement and inflation comprising a balloon having:

an elastomeric membrane having a proximal opening and an inner surface, a self-sealing valve comprising a valve body for receiving an inflation instrument to inflate the balloon, the valve body including:

a base portion bonded to the inner surface of the elastomeric membrane so as to seal the proximal opening of the balloon, an interior sealing portion extending distally from the base into the balloon, the sealing portion being compressibly sealable in response to a pressure within the balloon following inflation of the balloon and removal of the inflation instrument;

further comprising a balloon dispenser for housing the balloon prior to receipt of the inflation instrument, the balloon dispenser comprising:

a balloon seating element sized to allow the balloon to rest in the seating element, a guideway channel for guiding an inflation instrument into the dispenser and into mating alignment with the balloon, and an element responsive to external pressure for holding the balloon steady against longitudinal movement with respect to the inflation instrument.

2. The balloon system of claim 1, wherein the element responsive to external pressure for holding the balloon comprises a solid portion proximate to the balloon and being deflectable in response to external pressure so as to compress the balloon into the balloon seating element.

3. The balloon system of claim 2, wherein the element responsive to external pressure for holding the balloon further comprises one or more relief channels formed n the solid portion.

\* \* \* \* \*